United States Patent [19]

Alchas

[11] Patent Number: 4,998,926
[45] Date of Patent: * Mar. 12, 1991

[54] PARENTERAL FLUID ADMINISTRATION SET

[75] Inventor: Paul G. Alchas, Montclair, N.J.

[73] Assignee: Becton, Dickinson and Company, Franklin Lakes, N.J.

[*] Notice: The portion of the term of this patent subsequent to Aug. 28, 2007 has been disclaimed.

[21] Appl. No.: 474,180

[22] Filed: Feb. 28, 1990

Related U.S. Application Data

[63] Continuation of Ser. No. 809,093, Dec. 13, 1985, Pat. No. 4,952,210.

[51] Int. Cl.$^5$ .............................................. A61M 5/68
[52] U.S. Cl. ................................... 604/251; 604/257; 604/283
[58] Field of Search ............... 604/250, 251, 283, 264, 604/270, 247, 251

[56] References Cited

U.S. PATENT DOCUMENTS

| | | |
|---|---|---|
| 2,668,533 | 2/1954 | Evans . |
| 2,884,924 | 5/1959 | Shaw . |
| 2,999,499 | 9/1961 | Willet . |
| 3,242,920 | 3/1966 | Anderson .......................... 604/251 |
| 3,402,713 | 9/1966 | Stenkowski et al. . |
| 4,170,994 | 10/1979 | Komatsu ............................ 604/251 |
| 4,432,756 | 2/1984 | Urquhart . |
| 4,432,760 | 2/1984 | Mittleman et al. ................. 604/251 |
| 4,563,173 | 1/1986 | Ledley .............................. 604/247 |

Primary Examiner—Stephen C. Pellegrino
Attorney, Agent, or Firm—John L. Voellmicke

[57] ABSTRACT

A parenteral fluid administration set includes a non-vented adapter having a frusto-conically shaped recess therein for removably engaging the tapered tip of a vented container. The adapter includes a bore therethrough communicating with the recess. A drip chamber having an upper portion with a conduit therethrough and a flexible transparent body portion extending downwardly from the upper portion and terminating in a lower end, is provided. The upper portion of the drip chamber is connected to the adapter so that the bore and the conduit are in fluid communication. A flexible tube includes a first end connected to the lower end of the body portion of the drip chamber and a second end. Fluid delivery means for facilitating the delivery of parenteral fluid from the tube to the patient is connected to the second end of the tube.

14 Claims, 7 Drawing Sheets

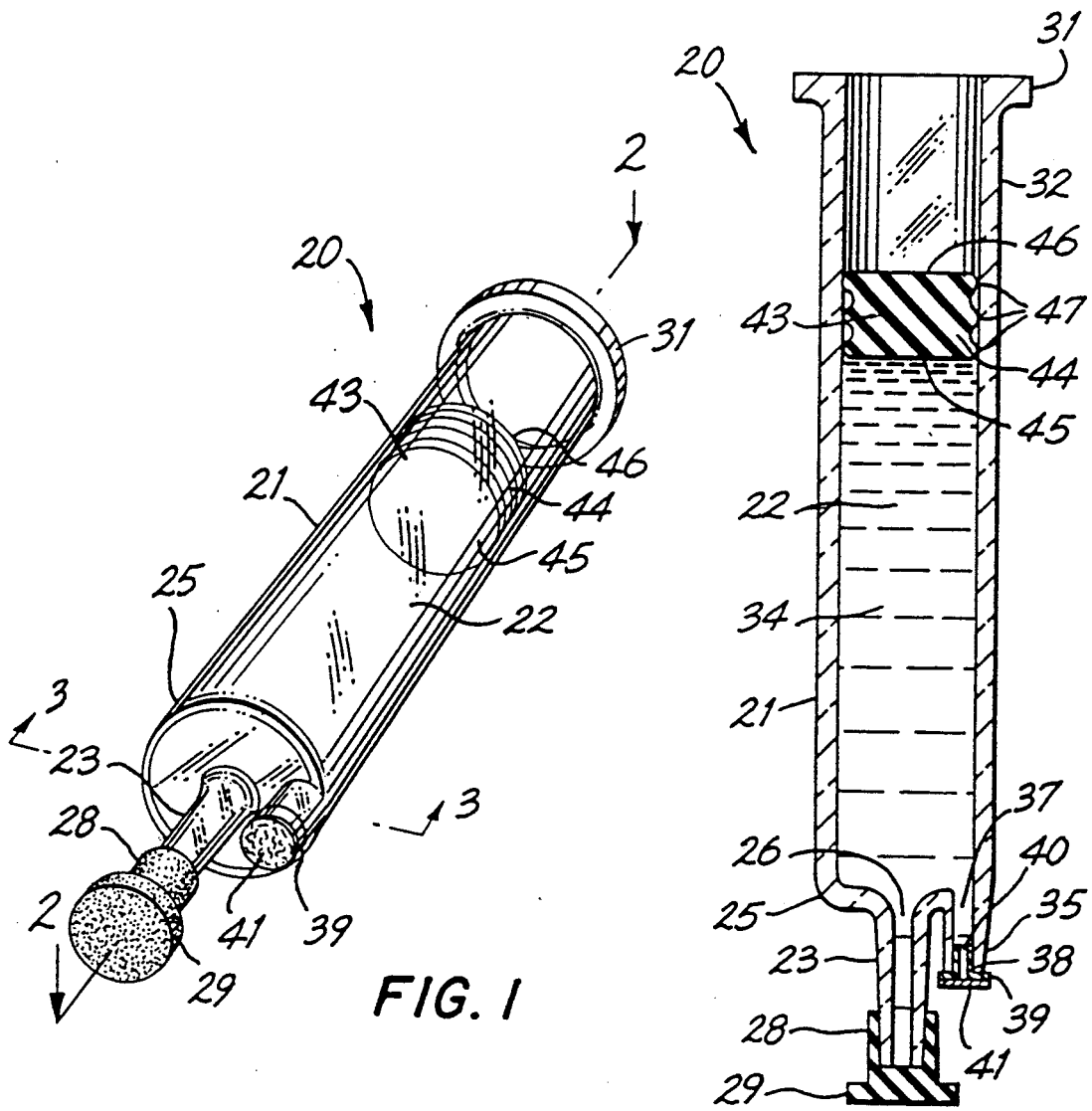
FIG. 1
FIG. 2
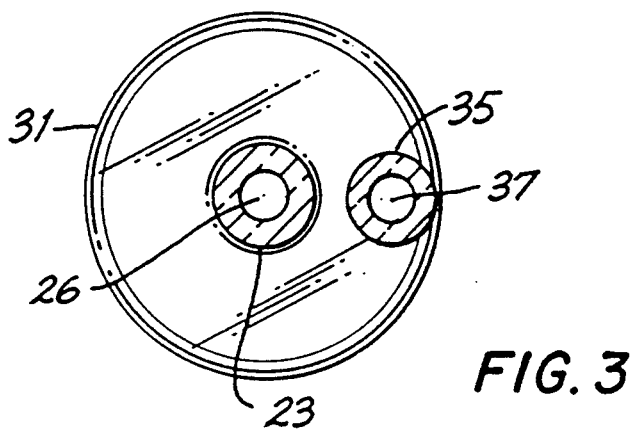
FIG. 3

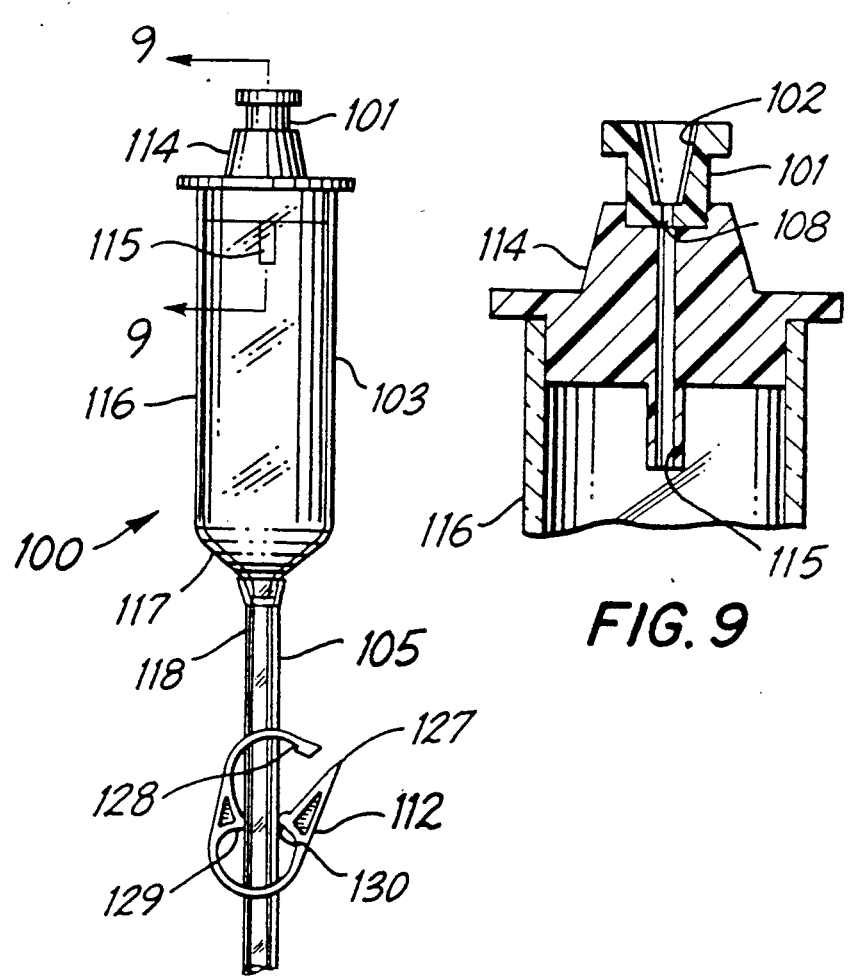
FIG. 9
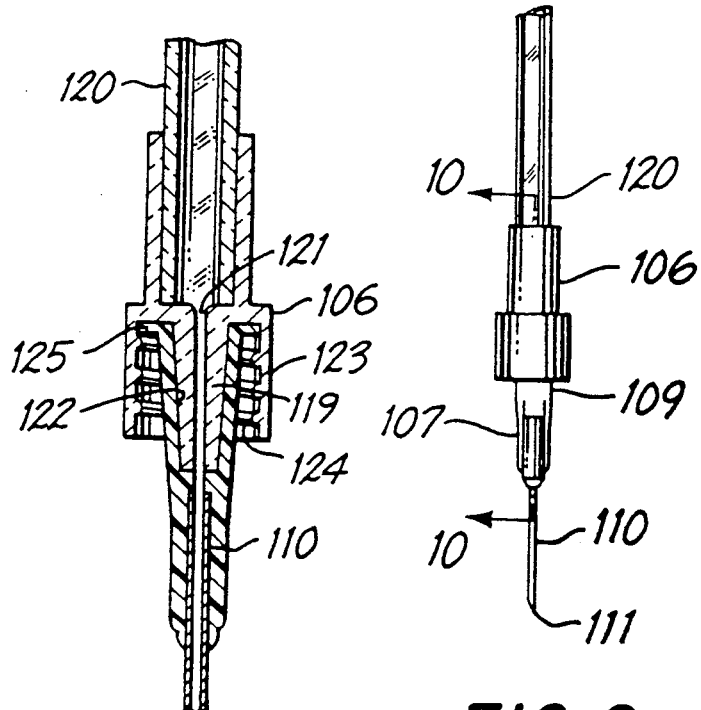
FIG. 10
FIG. 8

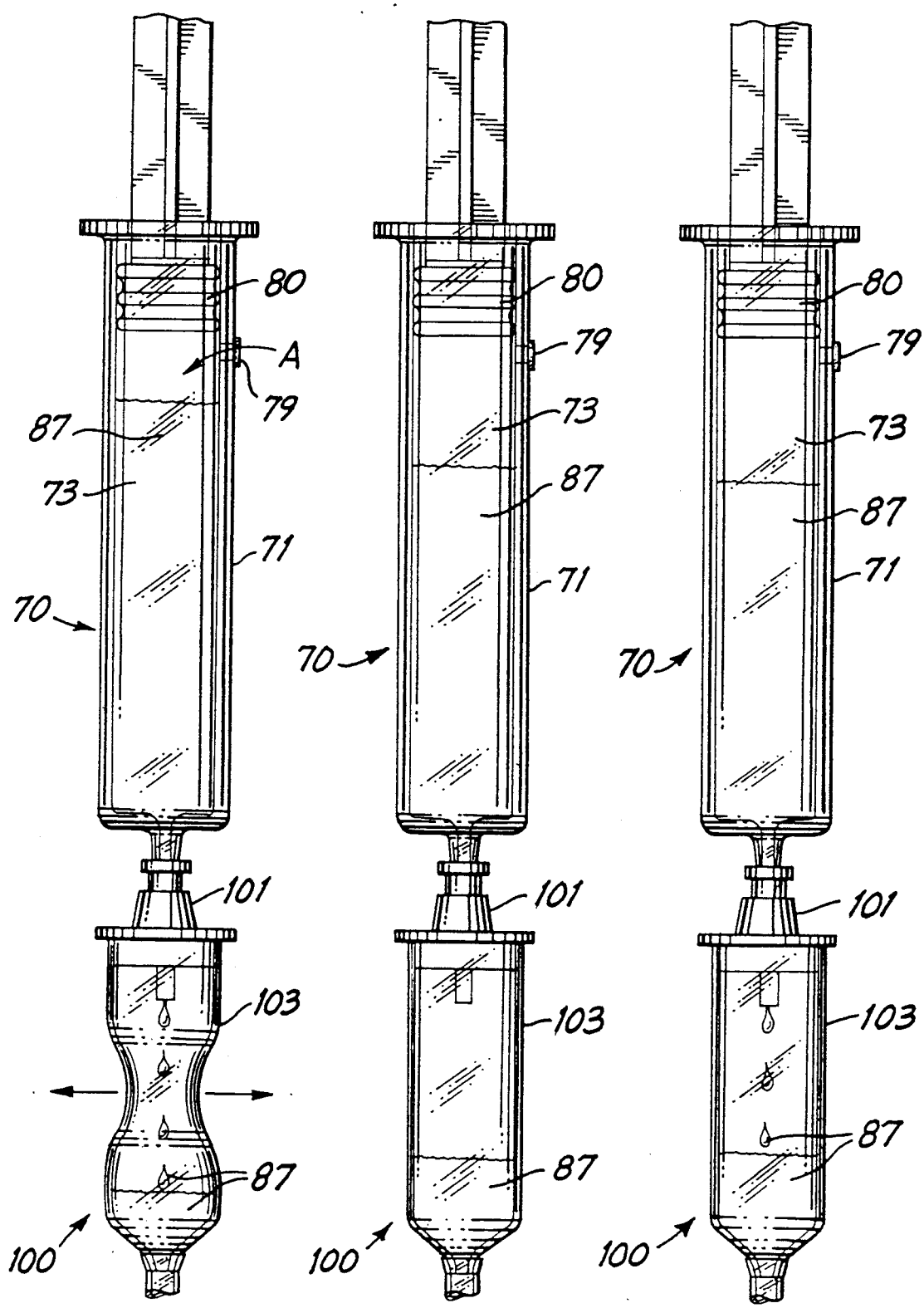

PARENTERAL FLUID ADMINISTRATION SET

This is a continuation of application No. 809,093, filed 12/13/85, now U.S. Pat. No. 4,952,210.

BACKGROUND OF THE INVENTION

1. Field of the Invention

The present invention relates to a container and an administration set for administering parenteral fluids and more particularly concerns a variable-volume vented container and a parenteral fluid administration set for the administration of parenteral solutions.

2. Description of the Prior Art

Parenteral solutions are routinely administered in patient therapy. A common example is the intravenous solution, such as sterile water or 5% dextrose in water, which is normally gravity fed into the patient's venous system from a bottle or bag reservoir through a transparent drip chamber, which provides visual evidence of the rate of flow of the solution, through a length of tubing into a needle or catheter, which is placed into the patient. An adjustable clamp is placed on the tubing and is used to deflect the tubing and change the flow rate of the solution.

Intravenous solutions contained in rigid bottles are commonly used with a vented adapter which has structure for establishing fluid communication with the interior of the bottle and usually includes a one-way valve which will allow air into the bottle to replace the liquid which has run out of the bottle through the I.V. tubing into the patient. Also, a filter is often provided to filter out airborne particles and possibly bacteria from the venting air entering the bottle through the valve. Such an adapter is taught in U.S. Pat. No. 2,668,533 to Evans.

If the bottle containing the intravenous solution includes venting structure, the adapter does not require a one-way valve or a filter, however, it will still include structure for providing a direct conduit from the interior of the bottle to the drip chamber as illustrated in U.S. Pat. No. 2,884,924 to Shaw. Also, if the I.V. solution is contained in a flexible bag an adapter without venting capacity may be used.

Most I.V. administration sets include a specific adapter for connection to a reservoir, a flexible transparent drip chamber, tubing, a clamp on the tubing, a "Y" site having a pierceable septum so that a secondary I.V. set can be attached, and an injection needle or catheter. Secondary intravenous setups usually include a smaller container or reservoir for administering medication such as antibiotics and vitamins. Secondary I.V. administration sets usually include an appropriate adapter, a flexible drip chamber, tubing and a needle cannula for piercing the septum at the "Y" site and establishing fluid communication with the primary I.V. set. In some secondary setups where flow rate is not critical, medication is injected directly into the I.V. line, as taught in U.S. Pat. No. 2,999,499 to Willet. More commonly, however, the secondary setup includes another flexible or rigid container for the medication, as illustrated in U.S. Pat. No. 4,432,756 to Urquhart et al.

Secondary intravenous medication containers are routinely prepared by the hospital pharmacy using specialized equipment and procedures which are sometimes unique for the secondary I.V. reservoirs. Some of the components such as, flexible reservoir bags, are expensive and some of the procedures are time consuming.

However, hospital pharmacies routinely fill syringes with liquid medication. The syringe is a low cost container and the equipment, such as a pipetter, and valve and tube sets, are readily available and easy to use efficiently. Quest Medical, Inc. of Carrollton, Texas presently markets an adapter similar to that taught by Evans in U.S. Pat. No. 2,668,533 referred to hereinabove. This adapter includes a filter and a one-way valve and a female luer fitting which allows the use of an ordinary disposable syringe as an I.V. container. The syringe is less expensive than other commercially available containers and is easily prepared by the hospital pharmacy. The cost of this secondary setup including the syringe is comparable to other secondary I.V. setups, however, savings may be achieved when more than one syringe is used with the same I.V. set.

Various parenteral solution reservoirs, such as vented and non-vented bottles, bags and syringes, and various I.V. setups some including one-way valves and filters and various other features have been addressed by the prior art, as alluded to above. However, there is still a need for a simple, straightforward, reliable, easily fabricated parenteral solution container which can be easily filled in a hospital pharmacy and can be used with a simple inexpensive I.V. administration set which does not include valves and filters.

SUMMARY OF THE INVENTION

An operable variable-volume vented container assembly of the present invention, for use in administering parenteral fluids, includes a housing having a chamber for retaining fluid. The distal end portion of the housing includes a passageway therethrough for communicating with the chamber. Venting means communicating between the chamber and the exterior of the housing, for allowing air to enter the chamber as fluid leaves the chamber through the passageway, is provided. The venting means includes an air-permeable liquid-impermeable means positioned to allow gases passing through the venting means to pass through the element. A stopper is slidably positioned in fluid-tight engagement inside the housing.

In accordance with another embodiment of the present invention, an operable disposable variable-volume container assembly for use in administering parenteral fluids comprises an elongate substantially cylindrical housing having a chamber for retaining fluid. A tip extends from a distal end of the housing and has a passageway therethrough communicating with the chamber. The tip is adapted to engage a parenteral fluid administration set so that there is fluid communication between the chamber and the administration set. Venting means communicating between the chamber and the exterior of the housing, for allowing air to enter the chamber as fluid leaves the chamber through the passageway, is provided. The venting means includes an air-permeable liquid-impermeable element positioned to allow gases passing through the venting means to pass through the element. The element is porous and capable of developing sufficiently high surface tension under liquid contact to serve as a barrier against liquid passage therethrough during normal use of the container assembly. A stopper is slidably positioned in fluid-tight engagement inside the housing and is capable of being moved by fluid pressure in the chamber. The fluid containing volume of the container is variable and related to the distance between the stopper and distal end of the housing. Closure means for releasably sealing the passageway is provided. A therapeutic liquid in the chamber is contained substantially between the stopper and the distal end of the housing.

In accordance with another aspect of the present invention, an operable vented receptacle for use in administering parenteral fluids comprises an elongate substantially cylindrical housing having an interior wall defining a chamber for retaining fluid. The chamber is adapted to accept a resilient stopper in slidable fluid-tight engagement therein. A tip extends from a distal end of the housing having a passageway therethrough communicating with the chamber. This tip is adapted to engage a parenteral fluid administration set so that there is fluid communication between the chamber and the administration set. Venting means communicating between the chamber and the exterior of the housing, for allowing air to enter the chamber as fluid leaves the chamber through the passageway, is provided. The venting means includes an air-permeable liquid-impermeable element positioned to allow gases passing through the venting means to pass through the element. The element is porous and capable of developing sufficiently high surface tension under liquid contact to serve as a barrier against liquid passage therethrough during normal use of the receptacle.

In another aspect of the present invention, a parenteral fluid administration set includes a nonvented adapter having a frusto-conically shaped recess therein adapted to removably engage the tapered tip of a vented container wherein the adapter includes a bore therethrough communicating with the recess. A drip chamber having an upper portion with a conduit therethrough and a flexible transparent body portion extending downwardly from the upper portion and terminating in a lower end is connected to the non-vented adapter so that the bore in the adapter and the conduit are in fluid communication. A flexible tube having a first end connected to the lower end of the drip chamber body portion and a second end connected to fluid delivery means for facilitating the delivery of parenteral fluid from the tube to the patient.

In another embodiment of this other aspect of the invention, a parenteral fluid administration set for use with a variable-volume vented container including a housing having a chamber for retaining fluid and a tip extending from the housing having a passageway therethrough communicating with the chamber wherein the tip is frusto-conically shaped having a smaller outside diameter at the distal end of the tip than at the proximal end of the tip includes a non-vented adapter having a frusto-conically shaped recess therein adapted to removably engage the tapered tip of the vented container. This non-vented adapter includes a bore therethrough communicating with the recess wherein the bore is positioned to allow fluid communication between the bore and the passageway in the vented container tip when the tip engages the recess. A drip chamber having an upper portion with a conduit therethrough is connected directly to the adapter so that the bore in the adapter and the conduit are in fluid communication. The drip chamber also includes a flexible transparent body portion extending downwardly from the upper portion and terminating in a lower end. A flexible tube has a first end connected to the lower portion of the transparent body portion and a second end connected to fluid delivery means for facilitating the delivery of parenteral fluid from the tube to the patient.

In accordance with the principles of the present invention a number of advantages and objectives are obtained. The present invention provides a simple, straightforward, reliable, easily fabricated variable-volume vented container assembly for the storage and administration of parenteral fluids. The instant invention provides an air-permeable liquid-impermeable venting means which eliminates the need for using adapters having one way valves and/or filters, as will become apparent hereinafter. The instant invention also provides a variable-volume container assembly which can be easily filled in the hospital pharmacy using known inexpensive filling devices, commonly used for filling hypodermic syringes so that additional equipment is not necessary. Another aspect of the present invention provides a simple, straight-forward, reliable, easily fabricated I.V. administration set for use with the variable volume vented container assembly and other vented container assemblies.

BRIEF DESCRIPTION OF THE DRAWINGS

FIG. 1 is a perspective view of the variable-volume vented container assembly of the present invention;

FIG. 2 is a cross-sectional view of the vented container assembly of FIG. 1 taken along line 2—2;

FIG. 3 is an enlarged cross-sectional view of the vented container assembly of FIG. 1 taken along line 3—3;

FIG. 8 is a side elevation view of a parenteral fluid administration set of the present invention for use with a vented container assembly;

FIG. 9 is a cross-sectional view of the parenteral fluid administration set of FIG. 8 taken along line 9—9;

FIG. 10 is a cross-sectional view of the parenteral fluid administration set of FIG. 8 taken along line 10—10;

FIGS. 12-16 are side elevation views of the vented container assembly of FIGS. 6 and 7 in use with a parenteral fluid administration set.

DETAILED DESCRIPTION

Figure 4:
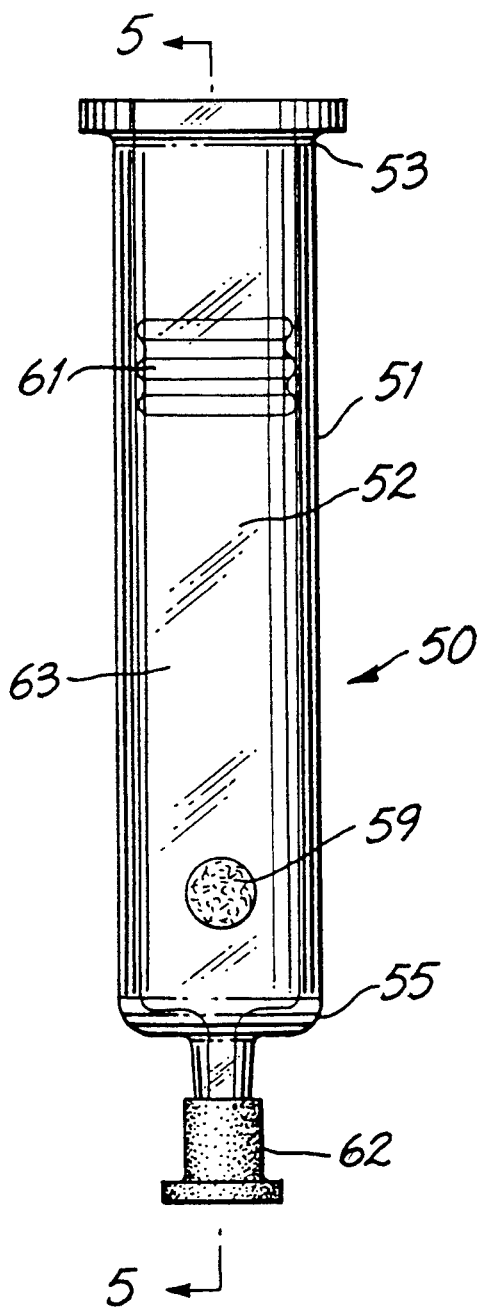
FIG. 4 is a side elevation view of an alternative embodiment of the variable-volume vented container assembly of the present invention.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1 through 3, an operable variable-volume vented container assembly 20 includes an elongate substantially cylindrical rigid barrel or housing 21 having a chamber 22 for retaining fluid. A tip 23 extends from a distal end 25 of the barrel and contains a passageway 26 therethrough communicating with chamber 22. For the purposes of the description of the present invention, the term "distal end" is meant to refer to the end of the housing which contains the tip portion or the passageway, whereas the term "proximal end" is meant to refer to the open end of the housing or the end furthest from the tip portion or the passageway. Tip 23 is preferably frusto-conically shaped having a smaller outside diameter at the distal end of the tip than at the proximal end of the tip. A preferably resilient closure or tip cap 28 is releasably connected to tip 23 and releasably seals passageway 26 in an air-tight manner. Tip cap flange 29 is provided to facilitate installation and removal of the tip cap. A flange 31 is preferably provided at proximal end 32 of the housing to facilitate handling the housing and suspending the housing in a vertical orientation for administering parenteral fluid 34 contained therein.

A venting nipple 35 is positioned at and extends from distal end 25 of the housing. The venting nipple includes aperture 37 for allowing air to enter chamber 22 as parenteral fluid leaves the chamber through passageway 26, as will be explained in more detail hereinafter. A circular plug 38, having flange 39 and conduit 40 is attached to the venting nipple. An air-permeable liquid-impermeable element 41 is attached to flange 39 so that gases passing through aperture 37 must pass through element 41. The air-permeable liquid-impermeable element is porous and capable of developing sufficiently high surface tension under liquid contact so that it serves as a barrier against liquid passage therethrough during the normal use of the container assembly.

Air-permeable liquid-impermeable element 41 is preferably a thin porous membrane having a maximum pore rating of preferably about 0.5 microns. This pore rating should be sufficient to entrap particulate matter including microorganisms which may be found in the hospital environment in which the present invention is intended to be used. In addition to preventing liquid from leaving the container through aperture 37, the air-permeable liquid-impermeable element allows air to enter chamber 22 through element 41, conduit 40 and aperture 37 to replace liquid which, when the instant invention is in use, flows out of the chamber through passageway 26. In the preferred embodiment, element 41, because of its 0.5 micron pore rating, can filter out microorganisms and prevent these microorganisms from entering the parenteral fluid which will be transmitted to the patient. In addition, some fluid medicaments, which can be used with the present invention, such as in chemotherapy, contain ingredients which should be contained within the fluid system and not allowed to enter the surrounding environment. To this end, element 41 is also very useful.

Also, as will be explained in more detail hereinafter, element 41 may be attached to the flange portion of plug 38 via heat sealing, adhesive or other suitable means. Further, plug 38 is connected to venting nipple 35 via an interference fit between the outside diameter of the plug and the inside diameter of aperture 37, or by use of adhesive, ultrasonic welding or other suitable means. It will be apparent to one skilled in the art that numerous constructions can be used to cover an aperture in a housing with an air-permeable liquid-impermeable element and that the structure described hereinabove is exemplary of these many possibilities. It is within the purview of the present invention to include a structure similar to plug 38 but with a larger conduit so that it takes the form of a cap and engages or is attached to the outside surface of the venting nipple rather than being positioned within the aperture as described hereinabove. Also, it is within the purview of the present invention to include the structure wherein the entire plug is made of air-permeable liquid-impermeable material which is attached to the venting nipple, or any manner of orifice containing structure, wherein the orifice is covered by an air-permeable liquid-permeable element so that air passing through the orifice must also pass through the element.

A resilient stopper 43 is slidably positioned in fluid-tight engagement inside the housing. The stopper outside diameter is larger than the inside diameter of the housing so that the stopper, when introduced into the housing, is compressed enough to provide adequate pressure between the housing and the stopper to seal this interface, but yet remains slidable within the barrel under the influence of fluid pressure in the chamber. Preferred stopper 43 includes a piston-like body 44 having distal end 45, a proximal end 46, and annular ribs 47 having an outside diameter larger than the inside diameter of the housing.

It is preferred that the vented container of the instant invention be assembled so that distal end 45 of the stopper is adjacent to distal end 25 of the housing. A known piston pump or pipetter may be used to fill the preferred vented container of the present invention by removing the tip cap and connecting the pump to tip 23 of the housing via tubing and a female luer adapter. The pump can be filled with the desired medication and set so that one stroke of the pump is the desired volume. When the preferred container is connected to the piston pump one cycle of the pump will force the desired amount of fluid through passageway 26 into the chamber. The fluid pressure will force stopper 43 along the inside of the chamber. Any residual air which may be present inside the chamber may pass through the air-permeable liquid-impermeable element so that the entire chamber is substantially filled with liquid. It may be necessary during the filling operation to orient the container so that the entrapped air is directed toward element 41. After the container is filled with the desired amount of parenteral fluid, the tip cap is replaced and the vented container may be placed in storage or delivered to the point of use and connected to a parenteral fluid administration set, as will be explained in more detail hereinafter. It should be noted that, because stopper 43 moves along the inside diameter of the housing as fluid is forced through passageway 26, the container of the instant invention can hold various volumes of fluid because the volume of the container is variable and is related to the distance between distal end 45 of the stopper and the distal end of the chamber.

Figure 5:
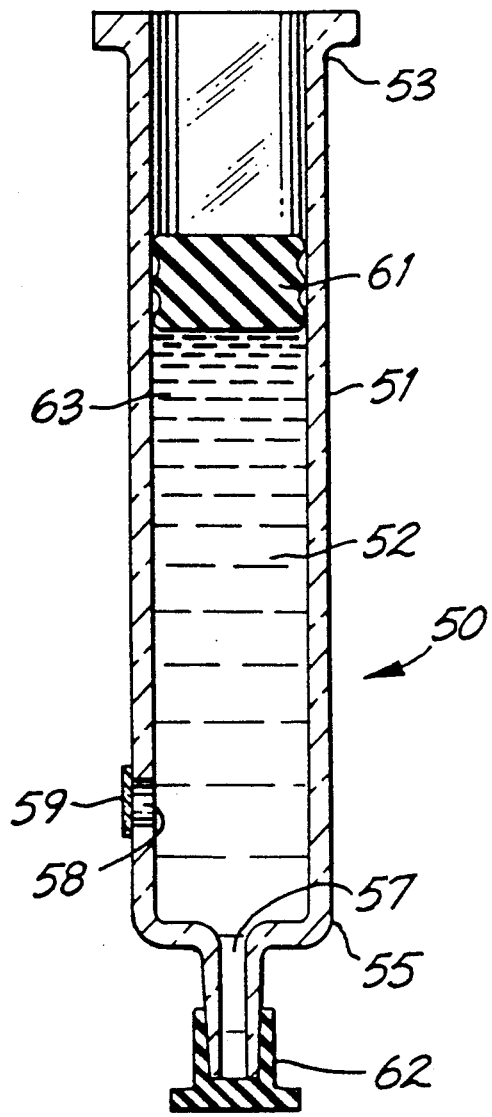
FIG. 5 is a cross-sectional view of the vented container assembly of FIG. 4 taken along line 5—5.

Referring now to FIGS. 4 and 5, an alternative variable-volume vented container assembly 50 of the present invention, for use in administering parenteral fluids, includes an elongate barrel-shaped housing 51 having a substantially circularly shaped cross section when viewed along its longitudinal axis, and having a chamber 52 for retaining fluid. Housing 51 includes an open proximal end 53 and a distal end 55 having a passageway 57 therethrough communicating with chamber 52. Venting means is provided for communicating between chamber 52 and the exterior of the housing for allowing air to enter the chamber as fluid leaves the chamber through the passageway. In this embodiment, the venting means includes an aperture 58 in the side wall of housing 51 extending between chamber 52 and the outside of the housing. Aperture 58 is covered by an air-permeable liquid-impermeable element 59 positioned so that all gases exchanged through aperture 58 pass through element 59. In this embodiment, element 59 is a sheet or membrane preferably having a maximum pore rating of about 0.5 micron for filtering particulate matter from gas passing therethrough so that the membrane serves as a substantial barrier against the passage of particles about 0.5 micron and larger, including microorganisms. It should be noted that it is also within the purview of the present invention to include a membrane shaped element covering the aperture in the housing from the inside. A carefully placed thin membrane could seal from the inside, possibly in a recess within the chamber, without substantially adversely effecting the operation of the container.

A resilient stopper 61 is slidably positioned in fluid-tight engagement inside the housing. Stopper 61 is capable of being moved by fluid pressure in chamber 52. The fluid containing volume of container assembly 50 is variable and related to the distance between stopper 61 and the distal end 55 of the housing. In this embodiment, element 59 is made of polymeric material and is attached to the outside diameter of the housing using adhesive, ultrasonic welding, heat sealing or other suitable means. A resilient closure or tip cap 62 releasably seals passageway 57 so that a therapeutic liquid such as parenteral fluid 63 is contained within chamber 52 until the time of use of the container assembly.

Figure 6:
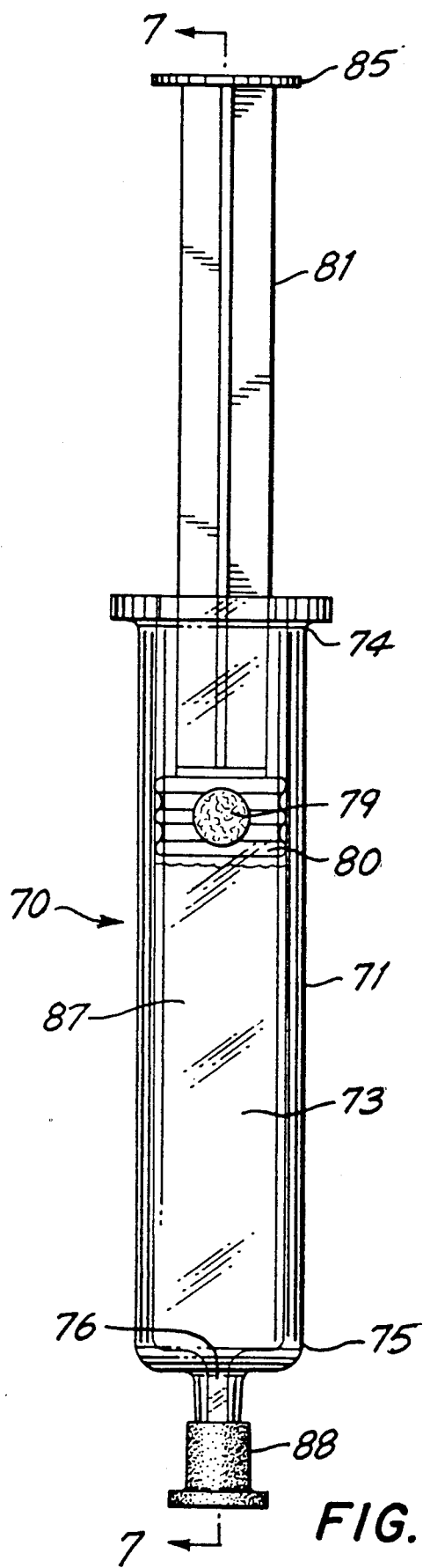
FIG. 6 is a side elevation view of another alternative embodiment of the present variable-volume vented container assembly of the present invention.
Figure 7:
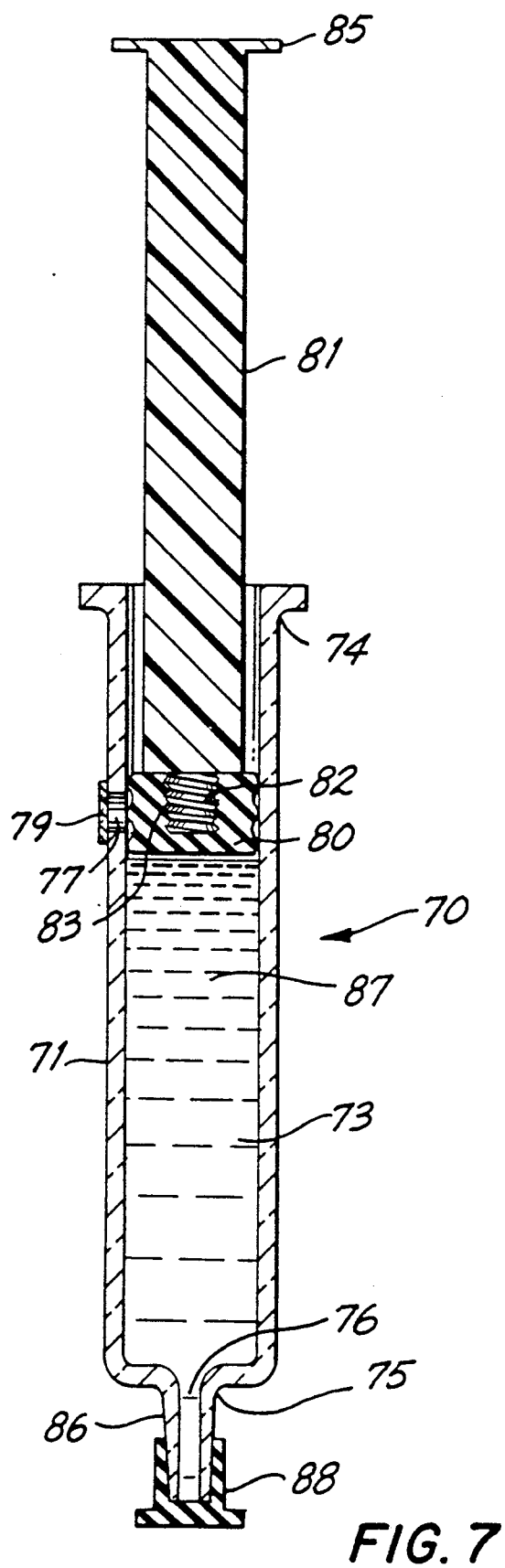
FIG. 7 is a cross-sectional view of the vented container assembly of FIG. 6 taken along line 7—7.

Referring now to FIGS. 6 and 7 another alternative embodiment of the present variable-volume vented container assembly 70, for use in administering parenteral fluids, includes a housing 71 having a chamber 73 for retaining parenteral fluid. Housing 71 has a substantially circularly shaped cross section, an open proximal end 74, and a tip 86 extending from a distal end 75 having a passageway 76 therethrough communicating with chamber 73. Tip 86 is preferably frusto-conically shaped having a smaller outside diameter at the distal end of the tip than at the proximal end of the tip. Tip 86 is preferably proportioned to accept standard available female luer fittings, which can be used as part of a parenteral fluid administration set, which will be discussed in more detail hereinafter. It is also within the purview of the present invention for the housing to include a circular internally threaded receptacle or collar concentric with and larger than the tapered luer tip. This type of fitting, i.e., the combination of a tapered luer tip and surrounding threaded receptacle or collar is referred to as as locking luer tip and is illustrated in U.S. Pat. No. 3,402,713 to Senkowski et al. The female locking luer fitting used with a locking luer tip has a tapered receptacle adapted to accept the luer tip, and wings projecting radially outwardly from the mouth of the receptacle so that the locking luer tip may be placed in the female locking luer fitting and rotated in a clockwise direction until the wings engage the threads in the collar and pull the tapered receptacle into tight frictional engagement with the tapered tip.

In this embodiment the venting means includes an aperture 77 through the proximal end of the housing extending between chamber 73 and the outside of the housing for allowing air to enter the chamber as fluid leaves the chamber through passageway 76. Air-permeable liquid-impermeable element 79 is positioned on the outside of the housing covering aperture 77 so that gases passing through the aperture pass through the element. Element 79 is porous and capable of developing sufficiently high surface tension under liquid contact to serve as a barrier against liquid passage therethrough during normal use of the container assembly. A stopper 80 is slidably positioned in fluid-tight engagement inside the housing. The stopper is capable of being moved by fluid pressure in the chamber. The fluid containing volume of the container is variable and proportional to the distance between the distal end of stopper 80 and the distal end of the barrel. Stopper 80 engages a rigid elongate plunger rod 81. In this embodiment, the stopper contains internal thread 82 which engages external thread 83 on the plunger rod, when assembled, as best illustrated in FIG. 7. The plunger rod extends outwardly from the proximal end of the housing and is accessible outside of the proximal end of the housing. Disc-shaped plunger rod flange 85 is provided as a convenient structure for applying force to move the plunger rod which will in turn move the stopper along the housing. The plunger rod can be installed when the container is assembled, or it may be provided as a separate unattached component which is engaged to the piston at the time the container is to be filled. It will be apparent to one skilled in the art that numerous constructions can be used to join a stopper and a plunger rod and that the arrangement described above is exemplary of these many possibilities. Also, it is within the purview of this invention to include a one-piece plunger rod-stopper assembly.

In this embodiment of the instant vented container assembly, the chamber can be filled with parenteral fluid without the use of an auxiliary pumping system. The user can connect tapered tip 86 of the housing to a conventional tubing adapter and tubing which is in turn placed in a reservoir of parenteral fluid. The user can now draw fluid into the chamber by moving the plunger rod, which in turn moves the stopper, away from the distal end of the housing until the desired volume of parenteral fluid 87 is contained within the chamber. At this point, resilient closure or tip cap 88 is placed on tip 86 to seal passageway 76. In this embodiment, the placement of aperture 77 near the distal end of the housing allows the parenteral fluid to be stored while not being in contact with the air-permeable liquid-impermeable element. Also, the placement of the element at the proximal end of the housing allows filling using the plunger rod rather than a pump. However, it should be noted that the plunger rod and stopper assembly can be used in other embodiments of the instant invention having an aperture and element located at the distal end of the housing. With these embodiments it will be necessary to cover the element, to prevent air from passing therethrough, while withdrawing the plunger rod and stopper to fill the chamber. It is within the purview of the present invention to include a removable cap or other removable sealing means for releasably sealing the venting means in an air tight manner so that air cannot pass therethrough during a filling procedure using subatmospheric pressure supplied by a plunger rod or similar device. Also, it may be possible to occlude a distally placed aperture using the operator's fingers.

Referring now to FIGS. 8-10, the variable-volume vented container assembly of the instant invention can be used in intravenous therapy procedures wherein various solutions, antibiotics, vitamins or other therapeutic liquids are transferred from the container assembly to the patient's venous system for absorption into the body. Another aspect of the present invention is a parenteral fluid administration set for use with a vented container such as the variable-volume vented container. Because the variable-volume vented container of the instant invention was not previously known to the art, parenteral fluid administration sets for use with this variable-volume vented container are required. A parenteral fluid administration set may be a primary intravenous (I.V.) set for delivery of intravenous fluid from the variable-volume vented container directly to the patient's body or a secondary I.V. set for delivery of parenteral fluid from the variable-volume vented container to a primary I.V. set which in turn delivers this fluid to the patient's body. Secondary I.V. setups are frequently used to administer medication to a patient by introducing the medication into a functioning primary I.V. setup. FIGS. 8-10 illustrate a parenteral fluid administration set in the form of a secondary I.V. set 100 for use with a vented container such as the variable-volume vented container. The secondary I.V. set includes a non-vented adapter 101 having a frusto-conically shaped recess 102 adapted to removably engage the tapered tip of the variable volume vented container. Adapter 101 has a bore 108 therethrough communicating with recess 102. A drip chamber 103 includes an upper portion 114 having a conduit 115 therethrough and a flexible transparent hollow body portion 116 extending downwardly from the upper portion and terminating in a lower end 117. Upper portion 114 is connected to non-vented adapter 101 so that bore 108 and conduit 115 are in fluid communication. It should be noted that it is also within the purview of the present invention to include an embodiment wherein the adapter and the upper portion of the drip chamber are integrally formed such as by injection molding to form a one-piece construction. It is also within the purview of the present invention to include members between non-vented adapter 101 and upper portion 114, such as flexible tubing, wherein the adapter in the upper portion are indirectly connected to each other through the flexible tube or other conduit means.

A flexible tube 105, preferably having a circularly-shaped cross section, has a first end 118 and a second end 120 wherein first end 118 is connected to lower end 117 of the flexible transparent body portion so that there is fluid communication between the interior of the flexible portion and the interior of the tube. It is preferred that the lower end 120 of the flexible tube be connected to fluid delivery means for facilitating the delivery of the parenteral fluid from the tube to the patient. In a secondary I.V. setup the fluid delivery means can include a male luer adapter or a male locking luer adapter 106 having a tapered tip 119 having a fluid channel 121 therethrough. The tapered tip is adapted to engage a hypodermic needle assembly 107 and to establish fluid communication between the needle assembly and tube 105. Hypodermic needle assemblies are known to the art and commercially available. A hypodermic needle assembly usually includes a hub 107 and a hollow needle cannula 110 having a sharpened distal tip 111 and projecting outwardly from the hub. Hub 107 includes a frusto-conically shaped tapered recess 122. Tapered hub recess 122 is adapted to removably engage the conventional tapered tip of male luer adapters or male luer fittings which are conventional and known in the art. The engagement of the hub to the luer adapter is via a frictional interference fit. Adapter 106 is of the form known as a locking luer fitting in that in addition to the tapered tip it has a collar 123 positioned concentrically around the tip wherein the inside of the collar contains a threaded projection 124 which is adapted to engage tabs 125 on the hub. The hub may be engaged to the adapter by rotating the hub so that the tabs follow the threaded projection forcing the engagement of tapered tip 119 into tapered hub recess 122. The locking luer-type fitting is a stronger fitting because it not only obtains its strength from the frictional interference fit but also from the threaded engagement of the components. There is an uninterrupted fluid path extending between non-vented adapter 101 and needle cannula 110. It is within the purview of the instant invention to provide a parenteral fluid administration set which encompasses a wide variety of fluid delivery means connected to the flexible tube including a direct connection of a sharpened cannula to the flexible tube, and a wide variety of specialized adapters, and the arrangement described hereinabove is exemplary of these many possibilities.

A pinch-type closure means such as clamp 112 is operatively associated with tube 105 for selectively opening and closing the tube to the passage of fluid. In FIG. 8, clamp 112 is illustrated in an open position. By manually squeezing clamp 112 so that edge 127 engages recess 128 will cause projections 129 and 130 to squeeze the outside surface of tube 105 sufficiently to collapse the tube and prevent the passage of fluid therethrough. Clamp 112 may be easily opened or closed by simple digital manipulation.

In use, a secondary I.V. administration set is used in conjunction with a primary I.V. administration set. Primary I.V. administration sets usually contain most of the elements of a secondary I.V. administration set. In addition, the primary administration set will usually contain a "Y" site which includes a pierceable septum so that the sharpened distal tip of the hollow needle cannula of the secondary I.V. administration set may be inserted therethrough to establish fluid communication between the primary and the secondary I.V. administration sets. The fluid delivery means in a primary I.V. administration set usually includes a needle cannula which is inserted into an I.V. catheter assembly which is in turn inserted into the patient's vein. A primary I.V. set will also include flow control means operatively associated with the tube for varying the flow of parenteral fluid through the tube and, accordingly, into the patient.

Figure 11:
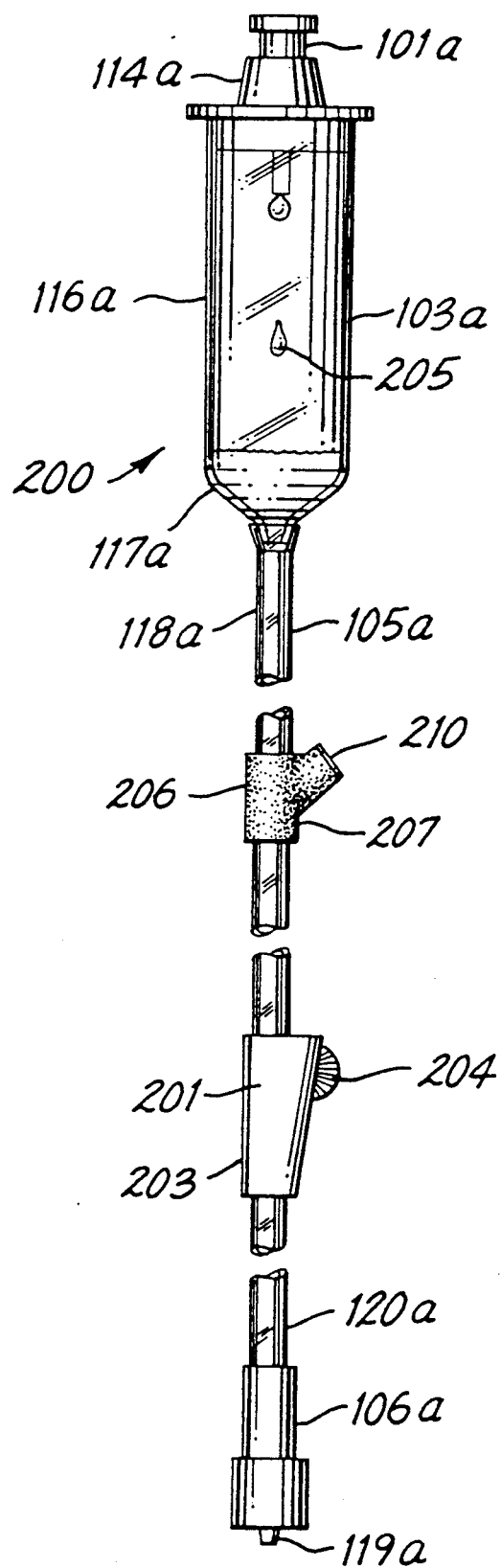
FIG. 11 is a side elevation view of another embodiment of a parenteral fluid administration set of the present invention.
Figure 12:
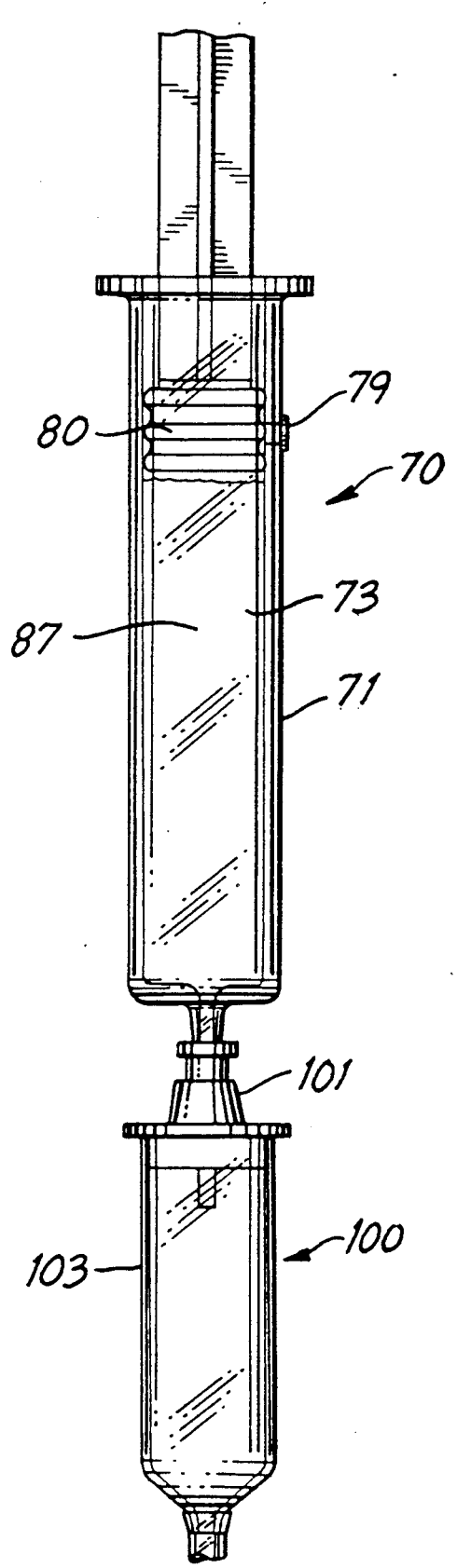

FIG. 11 illustrates an alternative embodiment of the parenteral fluid administration set of the present invention. This embodiment is a primary I.V. set for delivery of intravenous fluid from a vented container, such as the variable-volume vented container, directly to an I.V. catheter assembly (not shown) and into the patient's venous system. This alternative parenteral fluid administration set is a primary I.V. administration set 200 which includes components which are substantially identical to the components of the embodiment of FIGS. 8-10. Accordingly, similar components performing similar functions will be numbered identically to those components in the embodiment of FIGS. 8-10, except that a suffix "a" will be used to identify these components in FIG. 11. Primary I.V. administration set 200 is for use with a variable-volume vented container (not shown) having a chamber for retaining fluid and a frusto-conically shaped tip extending from the housing having a passageway therethrough communicating with the chamber. Primary I.V. administration set 200 includes a non-vented adapter 101a having a frusto-conically shaped recess (not shown) therein adapted to removably engage the tapered tip of the variable-volume vented container. The adapter includes a bore (not shown) therethrough communicating with the recess. A drip chamber 103a includes an upper portion 114a with a conduit (not shown) therethrough and a flexible transparent hollow body portion 116a extending downwardly from upper portion 114a and terminating in a lower end 117a. Upper portion 114a is connected to adapter 101a so that there is fluid communication between the adapter and the upper portion. A flexible tube 105a having a first end 118a and a second end 120a wherein the first end is connected to lower end 117a of the flexible body portion of the drip chamber. Fluid delivery means for facilitating the delivery of parenteral fluid from tube 105a to the patient is connected to the second end 120a of the tube. In this embodiment fluid delivery means includes a male locking luer type adapter 106a having a tapered tip 119a for removably engaging the hypodermic needle assembly or a catheter assembly, and establishing fluid communication between the needle assembly and the tube or catheter assembly. It is also within the purview of this invention to include other fluid delivery means such as a sharpened hypodermic cannula connected directly to the tube without any hub or connector means provided. The primary I.V. administration set 200 also includes flow control means operatively associated with tube 105a for varying the flow through the tube. In this embodiment, the flow control means includes a conventional roller clamp 201 including a housing 203 and a roller 204. This roller includes an axle-like projection (not shown) which rides in a recess (not shown) in the housing so that as the roller is rolled along the longitudinal axis of the housing the outside diameter of the roller compresses the outside diameter of tube 105a so that the roller is capable of squeezing tube 105a shut, not interfering with tube 105a and various positions therebetween. Accordingly, the roller is capable of changing the internal area of the tube available for the flow of parenteral fluid and, therefore, is capable of controlling the fluid flow rate through the tube. Fluid flow rate is controlled by positioning the roller along the housing and visually counting the drops of parenteral fluid 205 through the transparent body portion 116a of the drip chamber to determine the amount of parenteral fluid being delivered to the patient and adjusting this amount upwardly or downwardly by moving roller 204. It is also within the purview of the instant invention to include other means for controlling flow including other mechanical devices and electromechanical means for controlling the flow.

I.V. administration set 200 also includes access means in the form of a "Y" connector 206 connected to tube 105a between drip chamber 103a and roller clamp 201. Connector 206 includes connector housing 207 which interrupts tube 105a but allows uninterrupted flow along the tube. The interior of housing 207 is generally hollow and includes a port (not shown) covered by a pierceable septum 210 which is adapted to be pierced by a sharpened cannula to allow introduction of additional parenteral fluid into the primary I.V. set. Septum 210 is further adapted to seal itself upon the removal of the sharpened cannula.

It is desirable to include a one-way valve (not shown) along tube 105a between drip chamber 103a and "Y" connector 206 to allow fluid flow from the drip chamber to the "Y" connector but not in the reverse direction. As will be explained in more detail hereinafter, the one-way valve will terminate flow from the primary I.V. reservoir when the secondary I.V. reservoir applies more fluid pressure to the "Y" connector than the primary I.V. reservoir.

Figure 13:
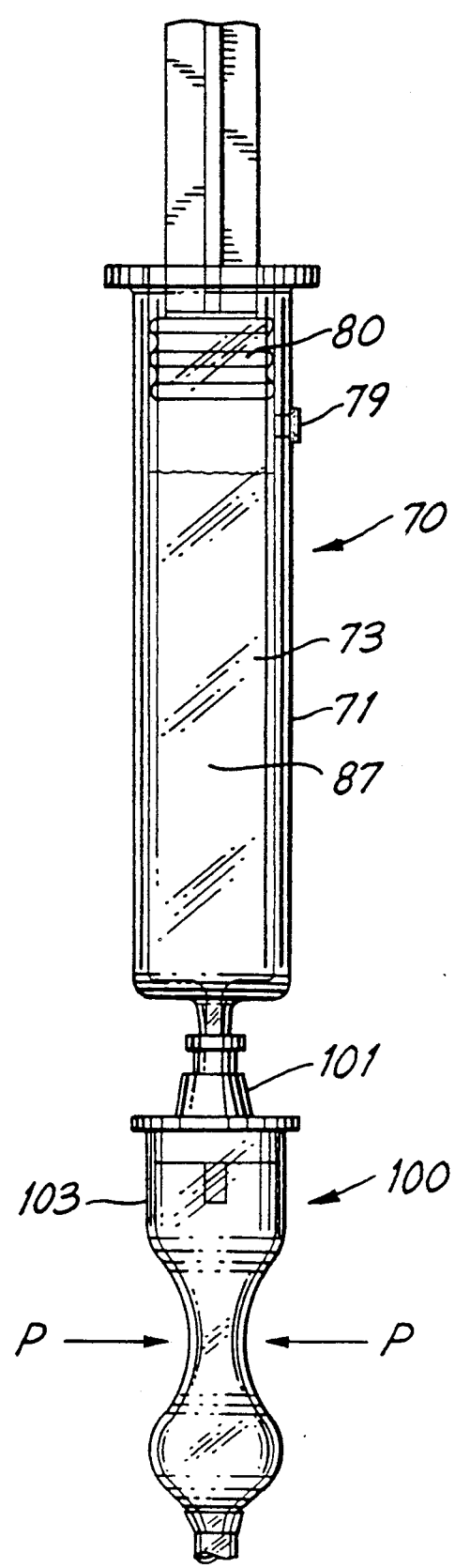

While the instant variable-volume vented container assembly may be used with a primary I.V. set 200 or a secondary I.V. set 100, the function of the variable-volume vented container and the I.V. administration set will be described herein, for purposes of simplicity, as being used as a source of parenteral fluid through the secondary I.V. administration set. FIGS. 12 through 16 illustrate the variable-volume container assembly of FIGS. 6 and 7 in use. As will become apparent hereinafter, the embodiments of FIGS. 1 through 5 can be used with a secondary I.V. set in a similar manner as the embodiment of FIGS. 6 and 7. In use, the user having a filled variable-volume vented container assembly and a secondary I.V. administration set closes the clamp on the secondary I.V. set, removes the tip cap from the filled container 70 and forces the tapered tip of the housing into tapered adapter 101 of the secondary I.V. set or if locking luer fittings are used the tapered tip is rotated into engagement with the adapter. At this time the user suspends the container assembly from an I.V. pole (not shown) or similar device, and lowers the source of primary I.V. fluid (not shown) so that the secondary container is in a higher position. Then, as best illustrated in FIG. 13, the user squeezes the flexible transparent drip chamber 103, applying force P to the drip chamber side walls. The pressure created by squeezing the drip chamber causes a pressure increase in the fluid system and further causes stopper 80 to move in a proximal direction exposing air-permeable liquid-impermeable element 79. Also, the squeezing force is repeated to start the flow of fluid from the vented container into the drip chamber as best illustrated in FIG. 14. The clamp (not shown) on the secondary I.V. setup is now opened and an additional squeezing action on the drip chamber will cause parenteral fluid 87 to flow through the entire secondary I.V. setup purging all air therefrom. The clamp is now closed and the container and the I.V. set appear as in FIG. 15. Next the cannula of the secondary I.V. setup is inserted into the pierceable septum of the "Y" site of the primary I.V. line and the clamp is then opened. Parenteral fluid will now flow through the secondary administration set, the Y-site of the primary set and into the patient. The higher fluid pressure of the secondary I.V. setup will force the one-way valve in the primary I.V. set to close thus temporarily terminating the flow of fluid from the primary I.V. reservoir, into the patient. The rate of flow may be adjusted by the variable clamp on the primary I.V. set. As parenteral fluid leaves the variable-volume vented container assembly, atmospheric air A will pass through air-permeable liquid-impermeable element 79 into chamber 73 to replace the volume of liquid which has flow out of the chamber. During use the stopper will not move and the volume described by that portion of the chamber between the distal end of stopper 80 and the distal end 75 of the housing will remain relatively constant. When element 79 is made with material having a maximum pore rating of about 0.5 micron, the air entering the chamber will be filtered of particulate matter and microorganisms, 0.5 microns and larger, so that the parenteral fluid is not contaminated by this particulate matter and microorganisms from the environment. Also, in some situations, parenteral fluids, such as certain antibiotics and chemotherapy solutions, contain potentially hazardous components or living organisms which must be contained within the syringe and not allowed to escape and contaminate the environment. Here again, the air-permeable, liquid-impermeable element of the present invention serves the useful purpose of protecting the environment from the components of the parenteral fluid which should remain isolated therefrom. When the parenteral fluid from the vented container is transferred to the patient another vented container may be attached. When the secondary system empties the one-way valve in the primary I.V. set will open so that the primary setup may resume the infusion of parenteral fluids therefrom into the patient.

The housing may be constructed of a wide variety of rigid materials such as metals, plastics, glass and ceramics. Plastic and glass are preferred due to their transparency and compatibility with many medication formulations. A wide variety of materials, such as natural rubber, synthetic rubber and thermoplastic elastomers, are suitable for the stopper with natural rubber and butyl rubber being preferred. The choice of stopper formulation will be dependent on compatibility with the parenteral solution being stored. If a plunger rod is used, a wide variety of materials such as plastics and metals are suitable for the plunger rod with thermoplastic materials such as polypropylene, polyethylene and polystyrene being preferred.

Air-permeable liquid-impermeable materials in thin sheet or membrane form, or in more substantial thicknesses which can be formed into plugs, are known and available. For example, W. L. Gore and Associates, Inc. of Elkton, MD produces filter material known as GOR-TEX® membranes which are capable of being air-permeable liquid-impermeable and also can be manufactured in a variety of pore ratings to allow filtration of microorganisms. A 0.5 pore rating is preferred, however, smaller or larger pore ratings may be desirable in specific circumstances. Air-permeable liquid-impermeable membranes are available in polymeric materials such as polytetrafluoroethylene, polyester, polyvinyl chloride, polypropylene, polyethylene and the like preferably ranging in thickness from about 0.003 to 0.010 inches (0.0076 to 0.0025 cm). It is also possible to laminate the air-permeable, liquid-impermeable membrane material to a backing sheet which will provide increased structural integrity and stability to the structure to help prevent the air-permeable liquid-impermeable element from being damaged during use. The element may experience pressure of about 3 psi when the drip chamber is being compressed. Some non-woven fabrics are suitable for this backing sheet in as much as they are porous and can be made relatively thin, while being strong. In this respect, and although other materials may be chosen, such non-woven materials may be selected from the group of materials consisting of polypropylene, polyethylene, and polyester. It is possible to choose a backing sheet material which has good heat sealing properties so that, with the plastic housing, the element may be heat sealed over an aperture in the housing. In this case the air-permeable, liquid-impermeable element can be chosen primarily for its performance characteristics and the backing sheet can be chosen for its processability characteristics to improve the overall structure of the assembled product. Also, the element, or the element laminated to a backing sheet, may be heat sealed or attached to a plug or cap having a conduit therethrough using any suitable means. The plug or cap could then be forced into or over, or in some other way attached to the aperture in the housing during the assembly process. This form of manufacture may be desirable because in cases where the element is not properly attached only the plug will have to be discarded and not the entire housing.

A wide variety of rigid materials are suitable for the various rigid components of the parenteral fluid administration set such as the non-vented adapter, the upper portion of the drip chamber, the luer adapter, etc., with thermoplastic materials such as polypropylene and polyethylene being desirable and ABS being preferred. The flexible tube is preferably made of extruded polymeric tubing with polyolefins and polyvinylchloride being preferred. The flexible transparent body portion of the drip chamber is preferably made of polymeric material such as polyvinyl chloride. The components of the parenteral fluid administration set may be joined together via the use of adhesive, heat sealing, ultrasonic welding or other suitable means. It is preferred that the fluid contacting surfaces of the vented container assembly and the parenteral fluid administration set be sterile, accordingly, all components should be chosen also for compatibility with the sterilization process being used.

Thus, it can be seen that the present invention provides a simple, straightforward, reliable, easily fabricated variable-volume vented container assembly for the storage and administration of parenteral fluids. The instant invention is inexpensive to manufacture and because of its air-permeable liquid-impermeable venting means the adapters used with the instant invention need not contain additional filters and valves. This is an important feature of the present invention because adapters containing valves sometimes become clogged or allow fluid to escape through the valve which, in either case, compromises the intravenous delivery. The instant invention provides a variable-volume container assembly which can be easily filled in the hospital pharmacy using known inexpensive filling devices commonly used for filling hypodermic syringes so that additional equipment is not necessary. The instant invention also provides a simple, straightforward, reliable, easily fabricated parenteral fluid administration set for use with the variable-volume container assembly and other vented container assemblies.

What is claimed is:

1. A non-vented parenteral fluid administration set and a vented container comprising:
   a vented container including a housing having a chamber for retaining fluid and a frusto-conically shaped tip extending from the housing having a passageway therethrough communicating with said chamber;
   a non-vented adapted having a frusto-conically shaped recess therein removably engaging the frusto-conically shaped tip of the vented container, said adapter having a bore therethrough communicating with said recess, said bore being positioned to allow fluid communication between said bore and the passageway in the vented container tip when the tip engages said recess;
   a drip chamber having an upper portion with a conduit therethrough and a flexible transparent body portion extending downwardly from said upper portion and terminating in a lower end, said upper portion being connected to said adapter so that said bore and said conduit are in fluid communication;

a flexible tube having a first end connected to said lower end of said body portion and a second end; and fluid delivery means for facilitating the delivery of parenteral fluid from said tube to the patient connected to said second end of said tube.

2. The parenteral fluid administration set of claim 1 wherein said tube has a substantially circularly-shaped cross section.

3. The parenteral fluid administration set of claim 1 wherein said non-vented adapter and said upper portion are integrally formed.

4. The parenteral fluid administration set of claim 1 wherein said fluid delivery means includes a male luer adapter having a tapered tip for removably engaging a hypodermic needle assembly and establishing fluid communication between the needle assembly and said tube.

5. The parenteral fluid administration set of claim 4 wherein said fluid delivery means includes a removable shield for protecting said tapered tip of said male luer adapter.

6. The parenteral fluid administration set of claim 4 further including a hypodermic needle assembly having hub means engaged with said male luer adapter, and a needle cannula projecting outwardly from said hub means.

7. The parenteral fluid administration set of claim 6 further including a needle shield removably engaging said hub means for protecting said needle cannula before use.

8. The parenteral fluid administration set of claim 1 wherein said fluid delivery means includes a needle cannula having a lumen therethrough in fluid communication with said tube.

9. The parenteral fluid administration set of claim 1 further including pinch-type closure means operatively associated with said tube for selectively opening and closing said tube to the passage of fluid.

10. The parenteral fluid administration set of claim 1 further including flow control means operatively associated with said tube for varying the flow of fluid through said tube.

11. The parenteral fluid administration set of claim 10 where said flow control means includes a conventional roller clamp.

12. The parenteral fluid administration set of claim 10 further including access means connected to said tube between said drip chamber and said flow control means for allowing introduction of additional parenteral fluid into said tube.

13. The parenteral fluid administration set of claim 12 wherein said access means includes a pierceable septum adapted to be pierced by a sharpened cannula to allow fluid to enter said tube through the sharpened cannula, said septum further adapted to seal itself upon the removal of the sharpened cannula therefrom.

14. The parenteral fluid administration set of claim 12 further including one-wa valve means operatively associated with said tube between said drip chamber and said access means for substantially preventing flow of parenteral fluid in a direction from said access means toward said drip chamber while allowing fluid flow from said drip chamber toward said access means.

* * * * *